US012608384B2

(12) United States Patent
Zimmermann et al.

(10) Patent No.: US 12,608,384 B2
(45) Date of Patent: Apr. 21, 2026

(54) METHOD AND SEARCH PLATFORM APPARATUS FOR PROCESSING SEARCH QUERIES DIRECTED AT A DATABASE CONTAINING MEDICAL SAMPLE DATA AND/OR SAMPLES

(71) Applicants: Fraunhofer-Gesellschaft zur Foerderung der angewandten Forschung e. V., Munich (DE); Universitaet des Saarlandes, Saarbruecken (DE)

(72) Inventors: Heiko Zimmermann, Sulzbach (DE); Andreas Kurtz, Berlin (DE); Antonie Fuhr, Berlin (DE)

(73) Assignees: Fraunhofer-Gesellschaft zur Foerderung der angewandten Forschung e. V., Munich (DE); Universitaet des Saarlandes, Saarbruecken (DE)

( * ) Notice: Subject to any disclaimer, the term of this patent is extended or adjusted under 35 U.S.C. 154(b) by 0 days.

(21) Appl. No.: 18/039,640

(22) PCT Filed: Dec. 11, 2020

(86) PCT No.: PCT/EP2020/085818
§ 371 (c)(1),
(2) Date: May 31, 2023

(87) PCT Pub. No.: WO2022/122172
PCT Pub. Date: Jun. 16, 2022

(65) Prior Publication Data
US 2024/0004887 A1      Jan. 4, 2024

(51) Int. Cl.
*G06F 16/00* (2019.01)
*G06F 16/2457* (2019.01)
(Continued)

(52) U.S. Cl.
CPC ....... *G06F 16/24578* (2019.01); *G16B 50/00* (2019.02); *G16H 10/20* (2018.01); *G16H 10/40* (2018.01); *G16H 50/70* (2018.01)

(58) Field of Classification Search
CPC ................................................. G06F 16/24578
(Continued)

(56) References Cited

U.S. PATENT DOCUMENTS

2017/0160535 A1*   6/2017   Mitra ..................... G16B 20/00
707/707
2020/0327250 A1    10/2020   Wang et al.
(Continued)

FOREIGN PATENT DOCUMENTS

DE          102019135380 A1      6/2021
JP             2004288094 A      10/2004
(Continued)

OTHER PUBLICATIONS

International Search Report for related PCT Application No. PCT/EP2020/085818 dated Sep. 1, 2021.

*Primary Examiner* — Alexandria Y Bromell
(74) *Attorney, Agent, or Firm* — Caesar Rivise, PC

(57) ABSTRACT
A method for processing search queries directed at a database containing medical sample data and/or samples from a multiplicity of samples of persons comprises the steps: entering a search query, with a request profile directed at retrieving at least one sample with sample data that have predetermined queried search parameters, into an AI processor device, searching for at least one selected sample using the AI processor device, the at least one selected sample satisfying the request profile at least with a specified probability, and outputting identification data of the at least one selected sample. A search platform apparatus that is configured to process search queries directed at a database (Continued)

containing medical sample data and/or samples from a multiplicity of samples of persons is also described.

18 Claims, 4 Drawing Sheets

(51) Int. Cl.
    *G16B 50/00*          (2019.01)
    *G16H 10/20*          (2018.01)
    *G16H 10/40*          (2018.01)
    *G16H 50/70*          (2018.01)
(58) Field of Classification Search
    USPC .......................................................... 707/723
    See application file for complete search history.

(56)                 References Cited

U.S. PATENT DOCUMENTS

| | | | |
|---|---|---|---|
| 2022/0245429 A1 | 8/2022 | Zimmermann et al. | |
| 2022/0292331 A1 | 9/2022 | Zimmermann et al. | |
| 2023/0021229 A1 | 1/2023 | Zimmermann et al. | |

FOREIGN PATENT DOCUMENTS

| | | | |
|---|---|---|---|
| JP | 2017142650 A | 8/2017 | |
| JP | 2018130408 A | 8/2018 | |
| JP | 2018533123 A | 11/2018 | |
| WO | WO2010032343 A1 | 3/2010 | |
| WO | WO2017042396 A1 | 3/2017 | |
| WO | WO2020233850 A1 | 11/2020 | |
| WO | WO2020233851 A1 | 11/2020 | |

* cited by examiner

Communication channel with real person/
enquiring authorised entities

Queries/
Training answers

Answer/
Training questions

AI of the ethical avatar

Shared public storage

Personal storage

History log of the training

Clock system

Research organisations/institutions/universities/platforms

Input (Query)

Output (Answer)

Ethical avatar

Training, monitoring, re-establishment of contact

Person

METHOD AND SEARCH PLATFORM APPARATUS FOR PROCESSING SEARCH QUERIES DIRECTED AT A DATABASE CONTAINING MEDICAL SAMPLE DATA AND/OR SAMPLES

CROSS-REFERENCE TO RELATED APPLICATIONS

This application is a U.S. National Phase Application under 35 U.S.C. § 371 of PCT/EP2020/085818, filed Dec. 11, 2020, the contents of which is incorporated herein by reference in its entirety.

BACKGROUND OF THE INVENTION

The present invention relates to a method and a search platform apparatus for processing search queries directed at a database containing medical sample data and/or samples from a multiplicity of samples of persons (in particular patients). The invention relates in particular to methods for using, and devices for establishing, an intelligent, self-learning platform that provides a multidirectional intermediary function between databases, for example in laboratories, biobanks and/or clinics, and the persons whose sample data and/or samples are stored in the databases, on the one hand, and research entities, such as research entities of the pharmaceutical industry and (bio)medical research organisations, on the other hand. The invention may be used for example in the operation of databases with sample data and/or samples from a multiplicity of samples of persons and/or in the processing of search queries, in particular by machine learning and/or artificial intelligence (AI).

In carrying out studies, for example for the purposes of research or surveys, interested research entities, such as companies in the pharmaceutical industry and/or (bio)medical research organisations, are reliant on samples and data of subject cohorts. A subject cohort comprises subjects who, for particular studies, have specific characteristics (parameters) such as a particular common disease profile and/or particular genetic commonalities.

Samples and data of subjects who would potentially be suitable for forming a cohort are available in medical laboratory facilities and/or biobanks. Entities seeking subjects have however hitherto had to expend great effort in searching through various medical laboratories and biobanks for the required data and patients. Legal constraints also apply: The entities are not allowed to, directly and without authorisation, access or use personal data, for example of patients.

Commercial medical laboratories and biobanks have a great interest in selling the samples and data that they possess, for example to enquiring research organisations. Genetic sequencing of the material is however necessary for this sale of particular samples, because only then can the research organisation determine the relevance of the corresponding sample to their own research. Full genetic sequencing however involves high costs, and great expenditure of time, for the corresponding laboratory or the biobank. Full genetic sequencing is therefore worthwhile only if the corresponding sample is also of interest for the research.

There is therefore an interest in developing a predictive tool that assists the organisations that possess the samples and data in identifying those samples for which expensive sequencing or other sample preparation is worthwhile.

It is generally known that a number of search engines with specific filter systems, such as the commercial provider iSPECIMEN, are available, which can be used by the industry and research sectors to find suitable patient samples. Such search engines can however operate only with standardised data in specific databases, and are not capable of making predictive statements. The enquiring research organisations can find only those samples which have been provided (tagged) with identifiers and for which genomic sequencing has already been performed.

Conventional search engines therefore cannot assist laboratories/biobanks in selecting which samples could be of interest for research (and for which, in particular, expensive genomic sequencing is worthwhile), nor can they, for the queries from the research organisations, generate information to make the formation of cohorts easier for the research organisations and to provide feedback to the laboratories/biobanks regarding those samples for which tagging is worthwhile.

SUMMARY

It is the objective of the invention to provide an improved method for processing search queries directed at a database containing sample data and/or samples from a multiplicity of samples of persons, and/or a corresponding search platform apparatus, with which disadvantages of conventional techniques are avoided. The processing of search queries directed at a database is intended in particular to make it possible to identify samples of interest more quickly and/or with less effort. The processing of search queries directed at a database is furthermore intended in particular to provide faster and/or easier access to the sample data and/or samples and/or to offer privacy protection for the persons to whom the sample data and/or samples pertain.

Said objective is achieved by a method for processing search queries directed at a database, and by a search platform apparatus, having the features of the independent claims. Advantageous embodiments and applications of the invention become apparent from the dependent claims.

According to a first general aspect of the invention, the above objective is achieved by means of a method for processing search queries directed at a database containing medical sample data and/or samples from a multiplicity of samples of persons, which method comprises the steps: entering a search query, with a request profile directed at retrieving at least one sample with sample data that have predetermined queried search parameters, into an AI processor device, searching for at least one selected sample using the AI processor device, the at least one selected sample satisfying the request profile, and outputting identification data of the at least one selected sample. The database is provided for example by a medical facility, a laboratory and/or a sample bank of biological samples (biobank). The request profile is preferably satisfied at least with a specified probability, which is determined by the function of the AI processor device.

According to a second general aspect of the invention, the above objective is achieved by a search platform apparatus that is configured to process search queries directed at a database containing medical sample data and/or samples from a multiplicity of samples of persons, wherein the search platform apparatus comprises an input device that is adapted to receive a search query with a request profile directed at retrieving at least one sample with sample data that have predetermined queried search parameters, an AI processor device that is coupled to the input device and is adapted to search for at least one selected sample, the at least one selected sample satisfying the request profile, and an output device that is adapted to output identification data of the at least one selected sample. The search platform apparatus or one of its embodiments is preferably adapted to carry out the method according to the first general aspect of the invention or an embodiment thereof.

The technique according to the invention advantageously offers more functions than a conventional search engine. It is a self-learning predictive tool with integrated artificial intelligence. This technique according to the invention can for example assist the pharmaceutical industry/(bio)medical research organisations in their search for patient cohorts suitable for studies, and can on the other hand assist database organisations, such as laboratories/biobanks, in evaluating for which of their samples it is worthwhile to invest, in particular working time and costs, to carry out sample preparations, for example genomic sequencing. This evaluation by the learning artificial intelligence (AI) of the platform can in turn be directly influenced by research entities by way of their queries.

With the invention, the queries from the research entities are advantageously digitalised and processed by the AI processor device. The AI processor device comprises a computer device that is adapted to use a program based on machine learning, for example at least one artificial neural network. The expression "AI processor device" will hereinafter also be used to refer to the artificial intelligence provided by the computer device. Methods for establishing an AI are described in WO 2020/233850 A1 ("Recursive coupling of artificial learning units") and WO 2020/233851 A1 ("Coupling multiple artificially learning units with a projection level"), which introduce not only the establishment of a learning system consisting of several AI units but also the storage and independent application of ethical principles/rules by AI systems.

The AI processor device learns by way of separate training and/or preferably by evaluating the queries directed at the AI processor device, and the associated identification results of the database.

According to a preferred embodiment of the invention, the AI processor device is used to search for a group of selected samples, all selected samples satisfying the request profile at least with the specified probability. The group of selected samples advantageously provides a limited number of samples in relation to the wide range of data stored, which number of samples can be processed further or inspected or output for the respective query, greatly reducing the effort involved in operating the database.

The method according to the invention or the search platform apparatus, respectively, preferably satisfies at least one of the following two functions:

a) Independently creating a ranking of the samples in accordance with relevance for the research b) Independently evaluating (rating) the parameters that are of interest for the research (which patient data are relevant to the research)

According to the first function, the identification data of the group of selected samples are preferably output with ranking information (placement information) that assigns each of the selected samples a probability of the request profile being successfully satisfied.

According to the second function, preferably additional rating search parameters are output, which match the search query such that a group of samples that have an increased probability of successfully satisfying the request profile can be selected. The rating search parameters particularly preferably include a genetic profile, data relating to clinical treatments, pre-existing diseases, familial predispositions to disease, personal diagnostic results, characteristics of living habits, eating habits, consumer behaviour, sport and physical activity characteristics, data relating to consumption of drugs or other intoxicants, data relating to medication intake, data relating to radiation exposure, epigenetic data, geographical information, age, gender, ethnicity, allergies and/or psychiatric disorders.

By contrast to conventional search engines, which are not influenced by the queries from the entities, such as research institutions, for particular sample profiles, and which also cannot transmit this information to the laboratories/biobanks, the AI processor device can be influenced, in particular trained, by the queries. Furthermore, conventional search engines are also not capable of independently outputting an evaluation (the rating) regarding which parameters of the patient data could be of interest for the research.

According to a preferred embodiment of the invention, the request profile from the research entities is directed at retrieving a group of samples with sample data, the persons associated with the group of samples forming a subject cohort. The subject cohort can advantageously thus be generated directly in response to the query.

According to a further advantageous embodiment of the invention, the AI processor device processes information from specialist literature, commercial market information from the industrial sector, in particular relating to pharmaceutical products, and/or information from approvals databases relating to pharmaceutical products.

The platform thus advantageously forms a search portal for the research entities that is of high practical value for the search for suitable patient cohorts, in that said platform transmits the search queries to the laboratories/biobanks. The queries, for example from the pharmaceutical industry, are used by the AI of the platform preferably in order to create the sample ranking. To create this ranking, the AI of the platform may monitor not only the queries from the pharmaceutical industry but also scientific literature. Not only can pharmaceutical concerns be placed in connection with suitable sample material via this platform, but it is also possible for academic, non-profit research organisations to use this platform. They in turn provide the platform with information regarding what fields of research will become popular. Aside from scientific publications, information from the industrial sector could also be of interest here: for example, what new medicines are entering the market, or what trends in pharmaceutical research can be observed from approvals databases. All of these entities (pharmaceutical concerns, non-profit research organisations, relevant publication landscape, development of new medicines etc.) influence the weightings in the ranking of the patient samples according to relevance within the AI of the device (see below, FIG. 1). With the aid of this information, the platform can (on the basis of its independently generated ranking) more successfully advise the laboratories/biobanks as regards which patient samples could be worth subjecting to expensive genomic sequencing. The AI of the device provides the advice on the basis of the sample ranking that it has generated on the basis of current research trends and queries from research organisations. With the aid of this analysis, the laboratories/biobanks reduce their initial sequencing costs.

Provision is preferably made for the search query to be converted into a fragmented search query using a coding function. The conversion is preferably performed by means of a coding device that is coupled to the AI processor device and to the input device.

In order to allow for data protection requirements, the following features are preferably implemented: The personal information of persons, such as clinical data or their genomic sequencing data, must not be freely accessible. These are subject to data protection. Nevertheless, a search for specific characteristics of the patient profile may be desired in order that the platform can operate optimally and can mediate between the two sides. This search may be performed through the use of the coding function, for example with a hash function: The platform itself has no insight into the genetic data of a patient but can, by way of hashes, search in the encrypted data within the databases of laboratories for suitable genetic profiles for the research entities, without knowing the specific genetic information. The coding function may be used in particular in accordance with the technique described in DE 10 2019 135 380.7 ("Method and data processing device for processing genetic data", unpublished on the priority date of the present disclosure), in which searches can be performed in inaccessible data (such as the genetic information of a person) in an encrypted manner (for example by way of hashes) without the need for all of the information of the data to be disclosed. DE 10 2019 135 380.7 is incorporated by reference into the present disclosure, in particular with regard to the processing of genetic data.

For this type of application, it is preferable for "secure enclaves" to be installed in the databases, via which the platform can transmit the queries from the pharmaceutical industry/research organisations with regard to particular samples by way of the coding function, for example the hashes. The database, for example the laboratory/biobank, confirms or denies the presence of suitable samples, without disclosing the underlying personal data. In this way, it is also not necessary for the platform to have personal patient data or a central ID system for the individual samples/patients. Instead, each presently relevant sample is stored in decentralised fashion and temporarily in encrypted (hashed) form (as in the case of disease alert apps). The device does not store the specific genetic data of particular samples, or the clinical patient data or other information relating to the patient profile. These personal data remain with the laboratory/biobanks, or with physicians and patients. The platform transmits the search in the form of queries converted using the coding function, in particular using "hashes", such that it does not need to gain direct access to these personal data.

In a preferred embodiment of the invention, consent of the associated persons to the use of data and/or samples is requested. The request for consent is particularly preferably responded to using questionnaires and/or informed consent documents and/or by an avatar apparatus.

It is preferably furthermore possible for information to be output, in particular to persons whose sample data are stored in the database, the output information particularly preferably relating to pharmaceutical products, diseases, research results and/or recommended actions.

The features disclosed in conjunction with the search platform apparatus and its embodiments likewise constitute preferred features of the method according to the invention, and vice versa. The abovementioned aspects and inventive and preferred features, in particular relating to the establishment of the search platform apparatus and the functions and configurations of the individual components that are described in conjunction with the search platform apparatus, therefore also apply to the method. The preferred embodiments, variants and features of the invention described above are combinable with one another.

Further details and advantages of the invention will be described below with reference to the appended drawings. The drawings schematically show:

DETAILED DESCRIPTION

Features of embodiments of the invention will be described below with reference to the configuration and functions of the search platform apparatus and of the avatar apparatus that is optionally coupled to the search platform device. Details of the AI processor device will not be described insofar as they are known from conventional techniques. An AI processor device may in particular be configured as described in WO 2020/233850 A1 ("Recursive coupling of artificial learning units") and WO 2020/233851 A1 ("Coupling multiple artificially learning units with a projection level"). WO 2020/233850 A1 and WO 2020/233851 A1 are incorporated by reference into the present disclosure, in particular with regard to the configuration of the AI processor device and its peripheral equipment, such as input and output devices and storages.

Search Platform Apparatus and Method for its Operation

Figure 1:
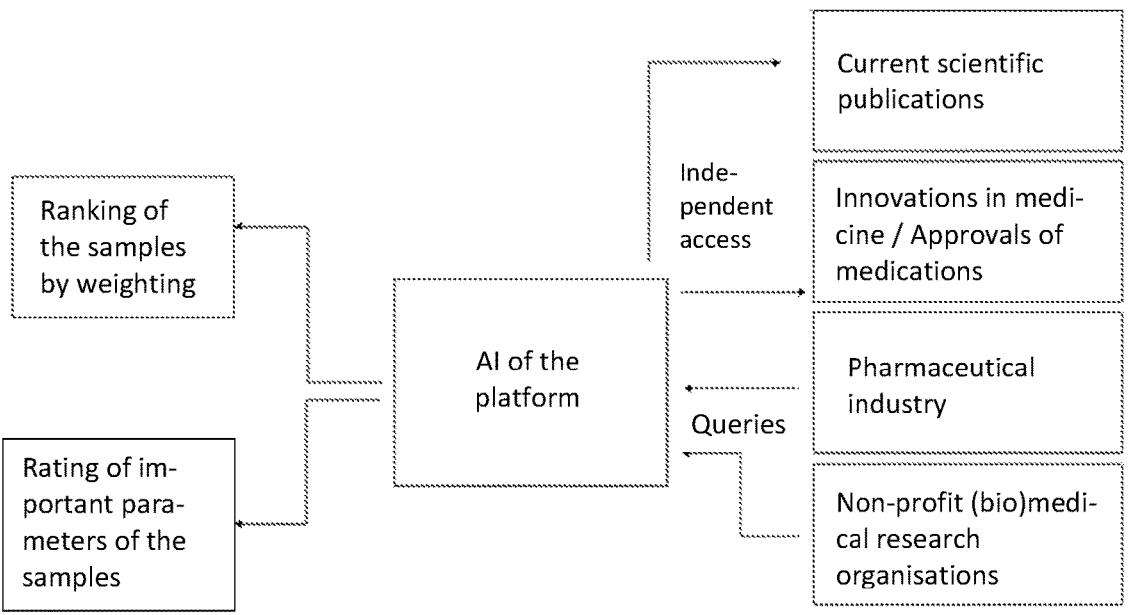
FIG. 1: an overview illustration of a search platform apparatus and of a search method with features according to preferred embodiments of the invention.

FIG. 1 illustrates the interaction of the AI processor device of the search platform apparatus with research organisations, approvals facilities and scientific institutions. The AI processor device, which is coupled to input and output devices (not shown), learns both from the queries from the pharmaceutical industry or from other research organisations and by accessing current scientific publications, innovations in medicine and/or information relating to samples which are of particular interest for the research, and which are accordingly provided with a weighting. The AI processor device furthermore learns in the same way to assess which parameters are of importance for the research, such as genomic characteristics, age, gender, living habits, pre-existing diseases and the like of the respective persons. By way of their queries, the enquiring entities influence the weighting with regard to ranking and rating.

Figure 2:
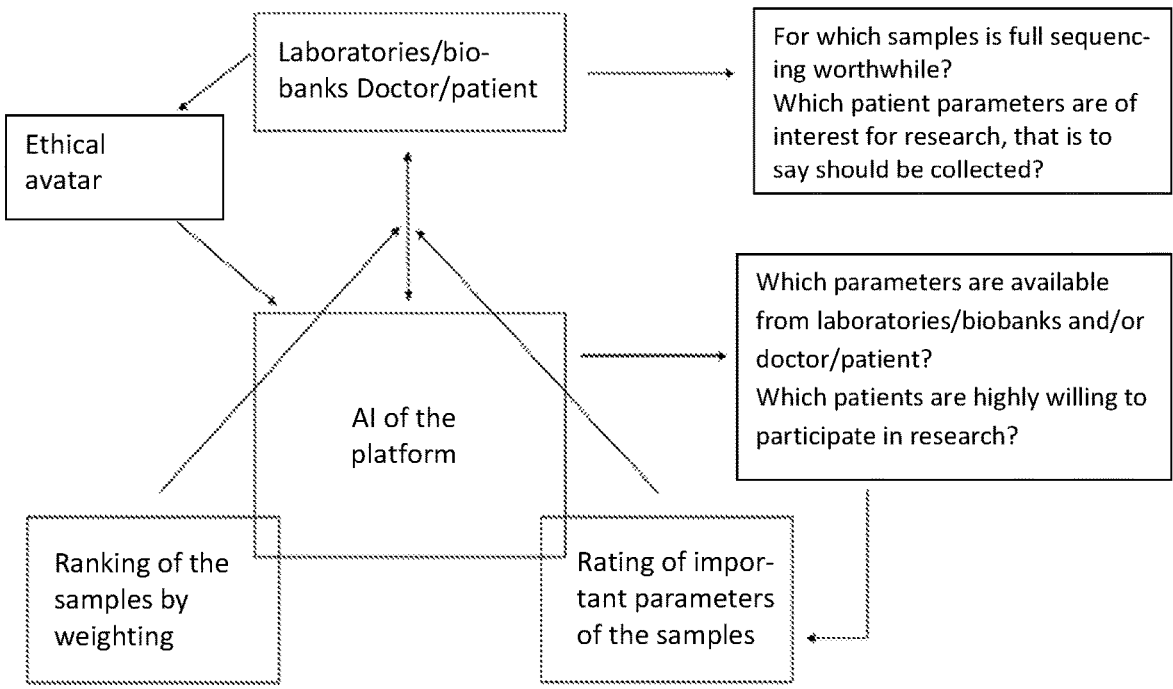
FIG. 2: further details of the functions of the search platform apparatus and of the search method according to preferred embodiments of the invention.

FIG. 2 illustrates the interaction of the AI processor device of the search platform apparatus with databases, such as laboratories/biobanks, and physicians/patients. By evaluating the queries from the research entities (FIG. 1), the AI processor device can provide information (identification information) for laboratories and biobanks as regards which samples will likely be worth subjecting to genomic sequencing, and which parameters are of interest to the research entities. Patients or physicians can also gather directly from the search platform apparatus where the current focus of research lies. The communication between the search platform apparatus and the database can take place fully anonymously and/or using coding functions, in particular hash functions, via secure enclaves within the laboratories/biobanks. An ethical avatar, which is described with reference to FIGS. 4 to 7, can be used as a digital representative of persons in order to assist the search platform apparatus in responding to queries (prediction of suitable samples), for example in order to ascertain whether a particular patient is available for participation in a study.

The search platform apparatus is advantageously capable of developing a ranking of samples (for example from "interesting" to "uninteresting", or based on probabilities of suitability), and identifying parameters that are of interest for the research, on the basis of the affirmative or negative answers from the databases (laboratories/biobanks) and/or on the basis of the search queries from the research organisations for particular profiles. Such parameters may for example include not only the genetic profile of the patient but also data relating to their clinical treatment, pre-existing diseases and familial predispositions to disease, personal diagnostic results, their lifestyle, eating habits, consumer behaviour, sport and physical activity, consumption of drugs, medication intake, any radiation exposure, epigenetic data, geographical information, age, gender, ethnicity, allergies and/or psychiatric disorders. The search platform apparatus assists laboratories/biobanks both in assessing which of their samples are currently of great value for the research and in evaluating those parameters which will become of interest for studies and the collection of which could likewise be worthwhile for the laboratories/biobanks (see FIG. 2).

For the use of data/samples of patients, the voluntary consent of the patients concerned may be required. The ethical avatar could be used to make it easier to obtain these declarations. This avatar is an intelligent tool that has learned, and can simulate, the ethical attitudes of the real person. With the aid of this avatar, the platform would be capable of making a preselection with regard to the ethical background of particular data/samples for the pharmaceutical industry: Instead of having to contact real persons in order to enquire about their attitudes to particular options for the application and use of their data/samples, a considerably quicker preselection could be made by surveying their ethical avatars. The platform thus not only assists the pharmaceutical concerns (or non-profit scientific organisations) in searching for patients with a suitable genetic and medical profile, but also at the same time makes a preselection with regard to which of these patients exhibits a high probability of being highly willing to participate in R&D (research and development). The ethical avatar functions as a prediction unit for the willingness of patients to participate in studies, this being derived from their personal values or religious attitudes or cultural background.

The prediction of whether a patient is open in principle to participating in a study may however also be made, without an "ethical avatar", by way of an evaluation of corresponding questionnaires or informed consent documents by the AI of the platform.

The manner in which the search platform apparatus operates yields the following advantages for the parties involved:

Advantage for Persons Whose Samples and Sample Data are Stored, in Particular Patients The manner in which the platform operates fulfils all data protection requirements, in that no patient-related data have to be stored on the platform (see above: search using hashes). The interests of the patient with regard to the protection of their data and their privacy are thus optimally safeguarded.

Through efficient operation of the search platform apparatus, the patient is given the opportunity to participate in studies that could be important to them (for example because they relate to the patient's disease). The platform could also provide the patient with a link to important sources of information which relate inter alia to medicines that the patient is taking or which provide new research results relating to the patient's clinical picture etc.

Patients may also, if interested, establish direct contact with the platform and share personal information (such as behavioural or environmental data), for example by allowing access to data from various fitness apps. The patients could thus be linked to research projects for which they would be suitable candidates.

All of this requires a high level of willingness of the patient, but could provide them with the advantage of greater involvement in the most up-to-date study results and personalised access to personally relevant medical innovations. Advantage for Databases, in Particular Laboratories/Biobanks The AI processor device of the search platform apparatus processes large amounts of data (queries from the research organisations, current scientific publication landscape, approval procedures, current medical innovations) and evaluates said data, and is thus capable of making predictions as regards which samples could be relevant for the research. These predicted results are highly valuable to the laboratories/biobanks, because they can thus assess which samples in their possession would be worth subjecting to expensive full genomic sequencing. Sequenced samples in particular are of value for the pharmaceutical industry and (bio)medical research organisations, and it is therefore of great importance for laboratories/biobanks to sequence primarily those samples which will later also be purchased by research organisations. The platform thus assists in mediating between laboratories/biobanks and potential purchasers of samples. The platform however also assists laboratories/biobanks in assessing which parameters of samples should be collected in order to make them of interest for research organisations (these may include not only clinical or diagnostic data but also the abovementioned information such as age, gender etc.). From the ranking by the platform, laboratories/biobanks can assess which samples rough SNP sequencing could be advisable for, and which samples are considered to be of such relevance that full genomic sequencing is worthwhile (because it is highly probable that this sample will be purchased).

Advantage for Enquiring Entities, in Particular the Pharmaceutical Industry/(Bio)Medical Research Organisations The platform assists research organisations in assembling suitable patient cohorts, in that said platform transmits the queries from the research organisations for specific samples to the relevant laboratories/biobanks. Byway of their queries, the research organisations have an influence both on the weighting within the sample ranking and on the assessment by the AI of the platform as regards which sample parameters (for example the radiation exposure of the patient, their pre-existing diseases, their misuse of drugs or the like) should be considered to be of interest. Thus, by way of the platform, the research organisations can play a part in influencing, for their own purposes, the sequencing activities of the laboratories/biobanks and their focus on particular sample parameters.

Not only is the protection of personal patient data safe-guarded by this platform (see above), but the internal research matter of the pharmaceutical concerns, which they disclose to a certain degree by way of their queries, must be treated confidentially. The concerns certainly have no interest in publicising their present area of research, thus attracting uninvited competition.

Figure 3:
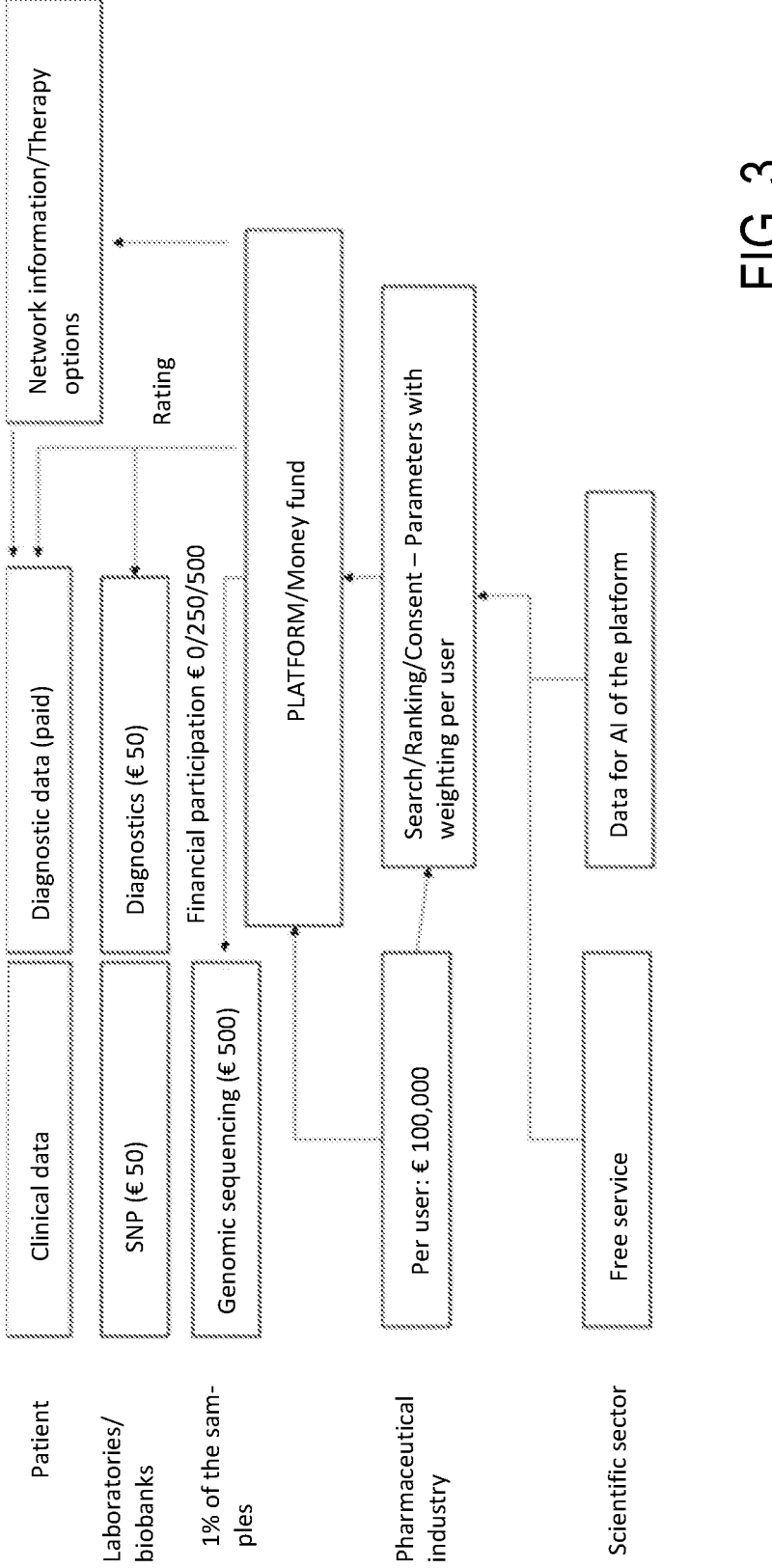
FIG. 3: an illustration of advantages of the use of the invention in practice.

FIG. 3 illustrates the advantages of the use of the search platform apparatus on the basis of a business plan. Users from the pharmaceutical industry pay a certain amount of money to use the search platform apparatus, for example EUR 100,000 per user. In return, the platform mediates between the user and laboratories/biobanks with samples that satisfy a request profile queried by the user, and the weighting of the sample ranking is influenced. This ranking has a direct effect on which samples are sequenced by laboratories/biobanks. In the case of particular samples that are relevant for research, the search platform apparatus may share the sequencing costs. Scientific non-profit research organisations can use the platform free of charge. The AI of the search platform apparatus advantages from the queries, because it can adapt its ranking to the present research interest on the basis of said queries. Patients who participate in studies, or who are also prepared to share personal data, may in return be placed in connection with relevant networks, which relate for example to their disease.

For example, genomic sequencing costs laboratories/biobanks around € 500. Laboratories/biobanks collect these costs only for approximately 1% of their samples. Carrying out relatively rough sequencing methods (such as SNPs) or diagnostic examinations costs approximately € 50 each time. The prediction by the search platform apparatus provides the laboratories/biobanks with valuable suggestions as regards which samples could be relevant for research organisations, such that the sequencing can lead to success more quickly, and sequencing costs can be used more efficiently.

Enquiring pharmaceutical concerns or other commercial organisations must, for queries directed at the platform, pay amounts of money (in the form of a "participation fee") into a fund, because any query has an influence on the ranking of the platform and the evaluation of parameters. Non-profit organisations such as university or other non-profit (bio) medical research organisations can submit queries free of charge. For the platform, the value of these queries lies in the information that they provide: from each query, the AI system of the platform learns which samples are currently popular in research, and can adapt its ranking and thus its predictions.

Enquiring laboratories/biobanks are provided with financial assistance from the money fund of the platform when they sequence particular samples that are evaluated in the ranking as being particularly relevant to research and they perform certain diagnostic work that provides parameters of interest for the research. In this way, laboratories/biobanks are motivated to sequence particular samples, which is in turn in the interests of the enquiring pharmaceutical industry/(bio)medical research organisations, which are thus provided with attractive sets of collated samples. Furthermore, the money in the fund of the platform is used for operating the platform (see FIG. 3 for an overview of the business plan).

The payment for the individual samples by the purchasing research organisations is made directly between the labora-tories and the research organisations; here, the search platform apparatus no longer plays a role.

Avatar Apparatus and Method for Use in Conjunction with the Search Platform Device The present invention also relates to an avatar apparatus ("ethical avatar") that is adapted to represent a person and to process personal data of the person, to an avatar system having multiple avatar apparatuses, to uses of the avatar apparatus, and to an avatar method for operating the avatar apparatus. The invention relates in particular to a method for developing, and a device for establishing, a virtual representative of a person, also referred to here as ethical avatar or as the avatar apparatus, wherein the avatar apparatus can for example learn and independently simulate individual moral attitudes, ethical principles, values and/or further opinions and interests of the persons. The invention may be used for example in the operation of databases with personal data of persons and/or in the processing of personal data, in particular by machine learning and/or artificial intelligence (AI), and/or in the processing of queries directed at the above-described search platform apparatus according to the invention.

Both in (bio)medical research and during the medical examination and treatment of persons (patients and/or subjects), a large amount of personal data relating to the patients or subjects is accumulated, be it through the giving of biological material (tissue samples, samples from somatic cells or stem cells) or in the course of the treatment of diseases (taking of biopsies, removal of tumours or the like). The personal data relate for example to the genetic information of the patient/subject, their disease history and/or any environmental influences to which they are exposed.

The administration and protection of such data require great expenditure on information technology, associated with the primacy of complying with ethical standards in the handling of this data (see the regulations for data protection and "informed consent").

Declarations of consent have hitherto been obtained from persons in writing, and anonymisation or pseudo-anonymisation of the identities of the patients/subjects has been used to protect sensitive data against unauthorised access by third parties. This necessary approach makes it very difficult or even impossible to survey the persons concerned at a later point in time. If situations change, new fields of research open up or there are uncertainties with regard to the opinion or the interests of the persons, it is no longer possible, or it is possible only with great difficulty, for the questions arising from this to be resolved by the persons concerned.

It is also the case in opinion research, in sociological or demographic analyses, in the course of Big Data studies (data science) and in the industrial/commercial sector that large amounts of personal data have to be processed as quickly as possible whilst safeguarding the privacy of the persons concerned; this has hitherto been very time-consuming and expensive.

In the field of personalised medicine, attempts are already being made to digitalise human body functions and body units (see for example the "Blue Brain Project" or virtual heart simulations). It is ever more common for digital versions of human body parts to be developed: it is sought to be able to virtually represent cells, organs or even entire individuals. This concept is referred to as "digital twinning"—a digital twin of the biological counterpart is generated.

Previous approaches have been limited to simulating physiological processes of the human. By contrast, mental response characteristics, such as moral attitudes, opinions, individual values and ethical principles of a person, have hitherto not been taken into consideration.

It is the objective of this sub-aspect of the invention to provide an improved data-based digital representation of a person, and/or methods for the use thereof, whilst avoiding disadvantages of conventional techniques. The digital representation of a person is intended in particular to allow additional information, and/or information in extended categories, such as non-physiological information about the person, to be provided, and/or for enhanced uses to be offered. The digital representation of a person is furthermore intended in particular to provide faster and/or easier access to statements from the person, and/or to offer protection for the privacy of the person.

According to the invention, an avatar apparatus, an avatar system with multiple avatar apparatuses, uses of the avatar apparatus, and an avatar method for operating the avatar apparatus, having the features described below, are used for this purpose.

Use is preferably made of an avatar apparatus that is adapted to represent a person and to process personal data of the person. The avatar apparatus comprises an AI processor device that is adapted for machine learning of individual mental response characteristics of the person by way of data training, wherein the AI processor device is configured to generate semantic answers (in particular at least one sentence or individual words, such as yes or no) in response to questions in a manner dependent on the mental response characteristics, a first storage device (personal storage) that is coupled to the AI processor device and is adapted to store the mental response characteristics of the person, an input device that is coupled to the AI processor device and is adapted to interact with the person and/or to receive questions relating to the person, and an output device that is configured to output signals that represent the answers generated by the AI processor device.

According to a further aspect, the use of the avatar apparatus or of one of its embodiments is preferably provided, wherein the use comprises at least one of the following: forming a multidirectional platform for placing medical laboratories and/or biobanks in connection with industrial companies and/or scientific research organisations, forming a platform for social research, opinion research and/or Big Data analysis, forming a platform for providing patient declarations, in particular declarations of consent to the use of personal data, forming a data protection platform, generating an advance directive of the person, providing input information for a synthetic biological procedure, and controlling technical systems.

According to a further aspect, to operate the avatar apparatus of a person, an avatar method is used, comprising the steps of receiving at least one question relating to the person, processing the question using the AI processor device, and outputting a semantic answer to the at least one question.

According to a further aspect of the invention, an avatar system that comprises multiple avatar apparatuses is used, wherein each avatar apparatus is adapted to a different use.

With the avatar apparatus, the mental response characteristics of persons are advantageously digitalised and/or simulated by the AI processor device. The AI processor device comprises a computer device that is adapted to use a program based on machine learning, for example at least one artificial neural network. The expression "AI processor device" will hereinafter also be used to refer to the artificial intelligence provided by the computer device.

The avatar apparatus advantageously provides a digital twin of the person to which the avatar apparatus relates, wherein the avatar apparatus represents for example individual opinions, interests and/or moral attitudes of the real person. The avatar apparatus advantageously makes it possible to simplify and/or speed up the administration of the personal data. At the same time, the avatar apparatus makes it possible to protect the privacy of the person concerned and to take their interests into consideration to a maximum degree.

The avatar apparatus according to the invention advantageously constitutes an intelligent, digital and predictively usable aid that can act as a representative of real persons. The avatar apparatus is for example usable as an advisory link between persons, on the one hand, and enquiring entities, such as research organisations or institutions or companies, on the other hand, wherein the anonymity of the person concerned is safeguarded (direct contact with the person is no longer necessary), and at the same time, the interests of the person can be represented in dealings with others. These advantages are described below, in particular with reference to the figures.

The avatar apparatus is advantageously a tool that can predict statements, in particular opinions, of its real counterpart and can be used in all forms of databases/analyses where it has hitherto been necessary to survey thousands of persons in a time-consuming and expensive manner.

The ethical avatar constitutes an artificial intelligence (AI) that is capable of being trained by persons in particular with regard to their moral attitudes, and of subsequently anticipating answers to newly posed questions on the basis of this training. During this training, the AI of the avatar learns the moral attitudes, values, interests and principles of the person. Using a learning, associative AI, the avatar can then use said principles/values/attitudes when answering new (ethical) questions. The avatar apparatus is thus capable not only of expressing what it has learned but also of intelligently and creatively applying what it has learned in new contexts. It can intelligently predict, on the basis of its knowledge of the person concerned, what the opinions and judgements of said person would be in response to questions in a particular new context.

The AI processor device is preferably adapted for machine learning of the individual mental response characteristics, which include moral attitudes, opinions, values, interests and/or ethical principles of the person. The response characteristics include subjective characteristics of the person that characterise how the person responds to a question, a fact, an experience, a situation, another person, a social group and/or a concept, wherein responses may include for example the articulation of statements, emotions and/or forms of behaviour.

In a preferred embodiment of the invention, the first storage device is configured to store the mental response characteristics in the form of catalogues of rules, micro-contracts and/or blockchains. The implementation of the invention is however not restricted to these variants but is also possible with other digitalisable formats.

Preferably, the first storage device is adapted to store individual additional data on which the mental response characteristics are dependent and which include in particular a religious affiliation, a group affiliation, an association membership and/or a party membership of the person.

According to a further advantageous embodiment of the invention, the AI processor device is adapted to understand and use ethically relevant expressions.

A second storage device (public storage, shared storage) is preferably provided, which is adapted to store general additional data that represent knowledge relevant to the mental response characteristics. The second storage device is particularly preferably coupled to an update device by means of which the general additional data can be updated.

According to a further advantageous embodiment of the invention, the avatar apparatus, in particular the input device, has a communication channel that is adapted for communication between the avatar apparatus and the person. This advantageously makes it possible for the person to access the avatar apparatus, for example in order to check the functioning thereof, to train the AI processor device, or to modify stored data.

Therefore, not only is the avatar apparatus trained by the person concerned, but the real person, whose moral attitudes the avatar apparatus simulates, furthermore preferably has the capability, at any time, to monitor and if necessary correct the statements, in particular decisions, made by their ethical avatar, to train the latter further, or to make changes to the stored values/interests/moral principles. The person however also has the option to transfer the decision-making authority entirely to, and allow themselves to be represented entirely by, their avatar.

The autonomy of the real person is advantageously not restricted, because the avatar functions merely as an assistive representative which is under the control of the person at all times and which merely performs advisory functions on the basis of the mental response characteristics, such as individual opinions and interests, of the person.

According to a further advantageous variant of the invention, the input device is provided with an authorising device that is configured to restrict the receipt of questions relating to the person to predetermined authorised entities, such as pharmaceutical companies and/or research organisations, and/or to predetermined allowable contents. The authorising device particularly preferably comprises a communication authentication storage and a standard communication protocol function.

In this embodiment, the protection of the personal data of the person is of particular importance: the avatar does not allow unauthorised parties to access the data, and also, when answering questions that are posed to it, provides personal data only to a limited extent and only to authorised entities.

The avatar apparatus preferably furthermore comprises a cryptographic storage that is adapted to store access keys. It is thus advantageously made possible for access to the avatar apparatus to be restricted in a highly reliable manner.

According to a further advantageous embodiment of the invention, the avatar apparatus has a log storage that is adapted to store a course of changes to the contents of the first and/or second storage devices.

Furthermore, a timer device may advantageously be provided, which is adapted to provide a timescale for the functions of the avatar apparatus.

The avatar apparatus particularly preferably comprises a communication device that is adapted to establish contact, and/or to communicate, with the person. This advantageously makes it possible, for example, for the semantic answer provided by the AI processor device to be verified.

The features disclosed in conjunction with the avatar apparatus and its embodiments likewise constitute preferred features of the method according to the invention, and vice versa. The abovementioned aspects and inventive and preferred features, in particular relating to the establishment of the avatar apparatus and the functions and configurations of the individual components that are described in conjunction with the avatar apparatus, therefore also apply to the method. The preferred embodiments, variants and features of the invention described above are combinable with one another.

Features of exemplary embodiments of the avatar apparatus will be described below with reference to the configuration and functions of the avatar apparatus. Details of the AI processor device will not be described insofar as they are known from conventional techniques.

Figure 4:
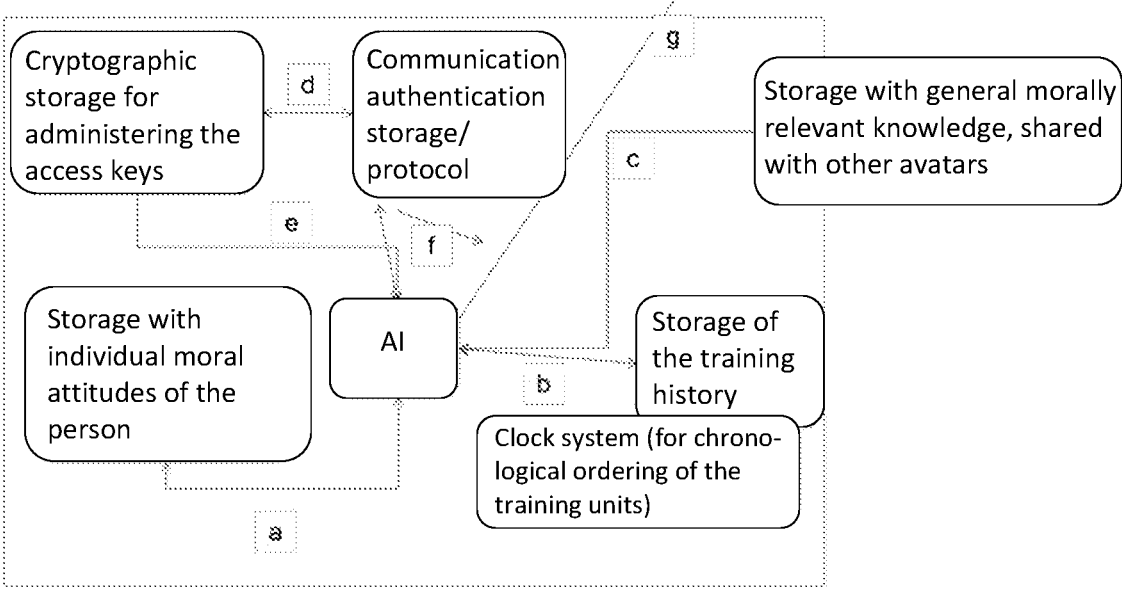
FIG. 4: an overview illustration of an avatar apparatus with features according to preferred embodiments of the invention.

FIG. 4 shows an embodiment of the avatar apparatus and the functioning thereof, wherein the sections (steps and/or components) a to g shown in FIG. 4 have the following meanings. Section a comprises storing the material that has been learned and/or accessing the material that has been learned, section b comprises logging the times of the training units, section c comprises accessing the second storage device in order to be able to make a survey more intelligent and compare same with a timer device (clock system), section d comprises an interaction between key administration and authentication storage, section e involves defining who is authorised to ask questions and/or receive information, section f comprises influencing the enablement or prevention of communication with the surroundings, in particular a communication protocol, and section g relates to a channel for the AI to be trained by a person, for the AI to be surveyed, and/or for the AI to provide information.

Figure 5:
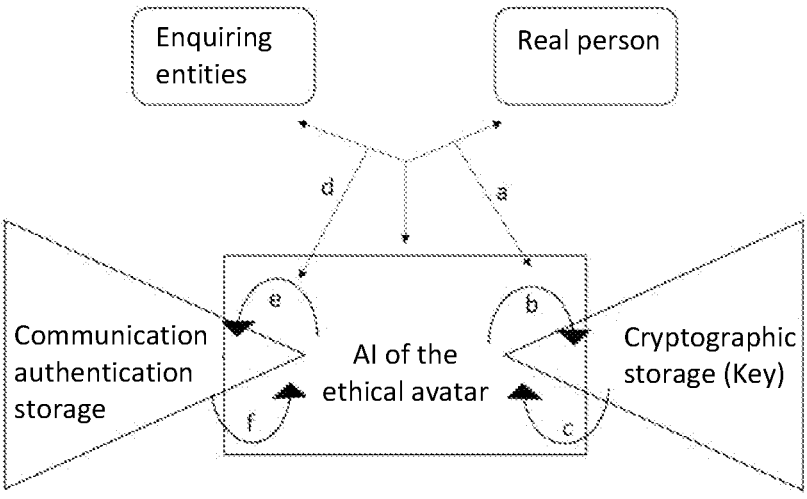
FIG. 5: an illustration of the communication, and of the monitoring of the communication, between the avatar apparatus and its surroundings (outside world)

The communication (see FIG. 7) and monitoring of the communication between the avatar apparatus and its surroundings (outside world, in particular enquiring entities or the real person training the avatar) comprises the following steps, as per FIG. 5. Step a is communication with the real person. In step b, the AI processor device uses its cryptographic storage to verify whether the person is authorised to make changes in, and/or to communicate with, the personal storage. In step c, yes/no decisions are made as to whether to allow training and/or yes/no decisions are made as to whether to provide information. Step d is a detailed query relating to a particular topic from an entity such as a research organisation. In step e, the AI processor device of the avatar uses a directory of all authorised entities in its communication authentication storage to check whether said AI processor device is authorised to provide information to said entity and on what topics said AI processor device is authorised to provide information to said entity, wherein, in particular, of a protocol of the communication in the communication authentication storage is used. In step f, the result of the check is provided.

Figure 6:
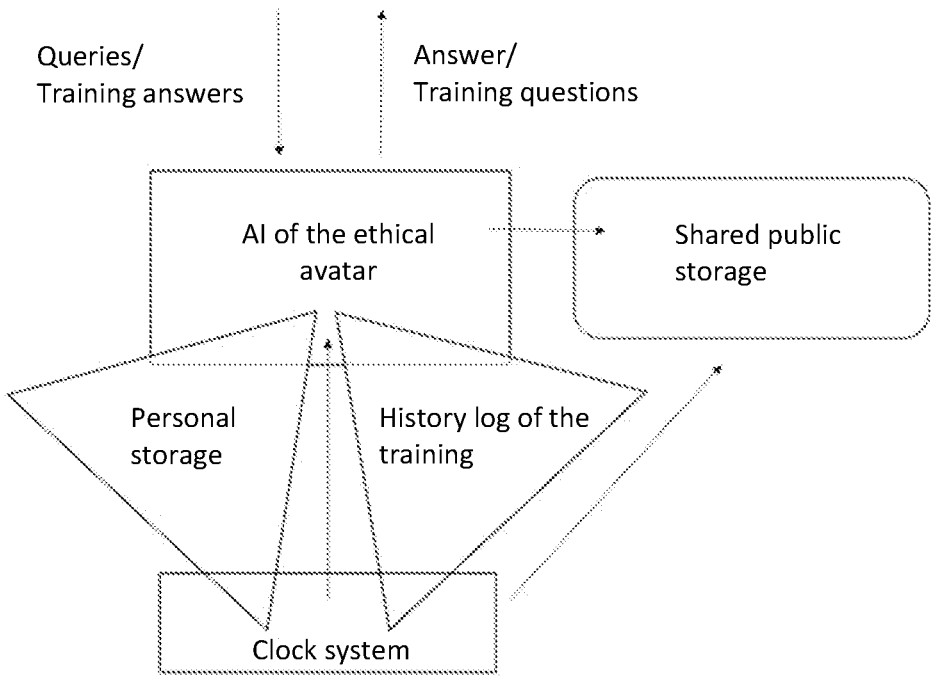
FIG. 6: an illustration of the use of the first and second storage devices.
Figure 7:
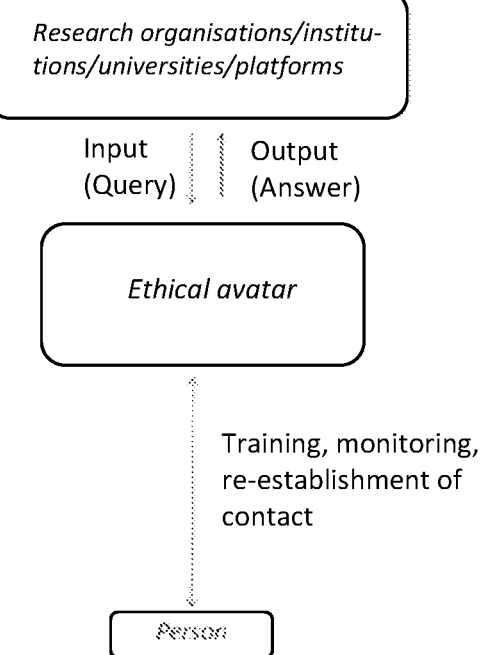
FIG. 7: an overview illustration of an avatar method with features according to preferred embodiments of the invention.

FIG. 6 illustrates the storage of data and the retrieval of data at the first storage device (personal storage) in combination with the use of the second storage device (shared public storage) for the purposes of chronologically ordering the training contents. The AI processor device of the ethical avatar is not only capable of storing the present mental response characteristics, for example moral attitudes/opinions/interests, of a real person in a personal storage and of accessing same (in the event of authorised queries, see FIG. 2) but can also store older versions of the mental response characteristics of the real person in a history log and place them in absolute chronological order using a clock system. This chronological assignment also allows alignment with the second storage device. The second storage device can furthermore use the AI processor device to make the training by the real person more intelligent, for example by virtue of the AI processor device asking for the religious denomination of the person and understanding the response "Christian" by accessing the second storage device, because it has been recorded in said second storage device what "being Christian" means with regard to the moral attitudes at a particular point in time.

The avatar apparatus has the following characteristics, illustrated in FIG. 4:

the avatar apparatus comprises (1) a learning component which, through personal training by real persons, can learn their moral attitudes, wherein (2) the results of this training are stored in the first storage device, and the AI of the avatar can access this information (the first storage device is not public, that is to say access from the surroundings of the avatar apparatus is blocked). The mental response characteristics, such as moral beliefs, of the person may be stored in the form of catalogues of rules, micro-contracts and/or blockchains in the first storage device of the avatar. Information relating to religious affiliation or group/association/party memberships of the person may be stored in the first storage device, and from these the ethical avatar is capable of drawing conclusions regarding the opinions of the person (by accessing a separate storage (second storage device, see (4)).

Furthermore, (3) the avatar apparatus is adapted to independently generate new answers (output) to new questions (input) on the basis of its stored knowledge relating to the mental response characteristics, for example attitudes, of the person. Such an avatar is preferably capable of understanding and using ethically relevant expressions, which is made possible by way of corresponding ontology (in particular systematic, formalised representation of entities, such as physical and abstract subjects, characteristics, facts, events, methods).

Aside from the first storage device for the moral attitudes of the person, the avatar (4) can preferably access a separate, second storage device, in which more fundamental knowledge that is relevant for the response characteristics, for example morally relevant knowledge, is stored (from prior professional training). This may for example be knowledge relating to various ethical theories and their implications, relating to religions or other groups (such as parties or associations) and their codes and rules, or else knowledge relating to ethically relevant expressions and ethical dilemma situations that are known and discussed in moral philosophy. Said second storage device (public storage, which is for example shared with other avatar systems) could be used by the avatar apparatus, during its training by persons, in order to survey the person more intelligently, to sensitise the person to particular questions, and to be able to categorise the answers from the person. The avatar uses this general knowledge only during the training, but not when answering ethical questions on behalf of its person at a later point in time. In this case, the avatar makes decisions only in relation to what it knows regarding the mental response characteristics, in particular individual values/interests/principles, of said person. The second storage device may be updated at regular intervals, for which purpose a clock system within the avatar (see (9)) is used.

(5), a communication channel is provided between the ethical avatar and its real counterpart, the person, such that said person can train the avatar and can, preferably at all times, monitor the behaviour of its digital representative and/or reopen the training if so desired. Communication with enquiring entities is likewise made possible, but is preferably subject to limitation. Preferably only the queries from authorised entities in authorised topic fields are allowed. The authorisation is performed (6) by way of a communication authentication storage together with a standard communication protocol function. This is a directory of those entities with which the avatar may communicate, together with conditions regarding what context the questions from the enquiring entity may relate to in order to be answered. The authorisations could be specified either by the real person themselves or by a central institution. Only authorised entities may receive information, within a clearly bounded scope: For example, an authorised medical organisation may survey the avatar, but only medical-related questions are allowed (representation of the communication between avatar and outside world in FIG. 5).

Using (7) a cryptographic storage in which access keys are administered, the avatar can preferably check what entity has what rights to receive information, and in what scope. Using this key, it is furthermore ensured that only the real person is authorised to make changes in the personal storage of the avatar.

Since the ethical avatar can be trained by the real person not only once, but said person can preferably make changes to the content of the personal storage at any time, the avatar (8) preferably comprises a storage (log storage) in which the historical course of the changes is stored (for example using blockchains or the like). Here, the avatar has (9) a clock system in order to allow chronologically absolute evaluation of the various training runs and alignment of same with the second storage device with regard to general morally relevant knowledge. In this way, the time of a particular training sequence $t_x$ can be assigned to the general state of knowledge at this exact time, as stored in the public, shared storage (see (4)). This can be of major importance for the understanding of the content of the respective training unit: For example, it can make a difference whether a real person has indicated that they feel bound to the codes of a particular community at a time $t_x$ or they do so at a time $t_{x+n}$ at which that community has reformed their codes. Both codes (the old version of $t_x$ and the reformed version of $t_{x+n}$) are stored in the second storage device (4) in a manner linked to the respective times, in the same way as the training units are stored in the personal storage (2) in a manner linked by way of the clock system to the training time. The personal attitudes of the person can thus be placed in absolute chronological order (illustration in FIG. 6).

The ethical avatar may furthermore (10) have a unit which relates to the availability, in principle, of the real person, which provides a link to a means of contact, or which makes statements relating to the contactability of the person.

In implementing the invention, there are in particular the following possibilities:

a) The real person has exactly one corresponding avatar apparatus (ethical avatar), preferably with a corresponding identification tag, at which queries can be directed by various entities. All information relating to said person is processed by means of one avatar apparatus.

b) A real person may be assigned multiple avatar apparatuses (avatar system) generated in various areas of application. Different avatars could be successfully synchronised with one individual either by way of an avatar identification number (provided by an avatar information entity), a global unique identifier (such as the patient ID or the biosample ID) or a (hashed) individual identifier (such as an image [for example, the concept of a "gravatar" has been developed—a gravatar is an image that accompanies the user from website to website and functions as an identifier (see https://de.gravatar.com)] or genetic "fingerprints" such as SNPs—single nucleotide polymorphisms—or STRs—short tandem repeats). If a person has several avatars, these avatars are preferably synchronised with one another in order that all avatars involved remain up to date with regard to the mental response characteristics, for example the attitudes and opinions, of their common real person. An alignment between the various avatars of a real person should be ensured.

Further details of specific exemplary embodiments and applications

1. Exemplary embodiments for Big Data analyses/data science

Avatars as part of a multidirectional platform that functions as an integrating link between medical laboratories/biobanks and pharmaceutical concerns and/or scientific organisations: Medical (commercial) laboratories have access to large amounts of data relating to clinical information, diagnostic results and genetic information of patients. They have an interest in the fact that this data can be utilised by the research and industrial sectors. On the other hand, the pharmaceutical industry and scientific organisations are, in their research, reliant on obtaining data from very specific patient groups. The mediation between these sectors is very complicated when using conventional techniques, but can be made easier using a platform with at least one integrated avatar apparatus. The platform brings together the information from both sides: it analyses which patients are being tested in the laboratories and, from the queries for patent profiles from the research sector, gains an insight into which of these data/samples from the laboratories are of interest to the research sector. The platform can thus assist both sides: It advises the laboratories on which samples/data would be worth subjecting to expensive full genomic sequencing (necessary for the research sector) (because the platform knows which samples/data are of interest for the research/industrial sector), and in so doing can assist the research sector in assembling suitable cohorts. The ethical avatars of the patients assist in this preselection, inter alia because they know the moral attitudes of their real counterpart. For the use of data/samples of patients, the consent of the patients concerned is required. Ethical avatars could be used to make it easier to obtain these declarations (see below).

Sociological research: Avatars could assist in the preselection of which persons could in principle be interested in which research topics and survey contents, or which persons would immediately lodge an objection.

Advantage: Fast and suitable preselection for sociological cohorts/survey groups.

Opinion research/Big Data analyses: In order to be able to easily and quickly collate and analyse the opinions of a very large number of persons, ethical avatars can be advantageous—not only do they assist in answering specific questions from opinion research institutions, but they also assist in evaluating the suitability of their persons for a corresponding survey in the first place (by assisting with the preselection).

2. Possible applications in a clinical context and in biomedical research

Provision of advice in connection with questions of informed consent: The avatar learns the person's answers to the questions of various declarations of consent, and is subsequently capable of anticipating said person's attitudes to new questions and answering on their behalf. The avatar performs the role of an advisory representative of the person, which has learned to answer on behalf of its person.

Advantage: Establishing direct contact with the person for questions relating to their declaration(s) of consent is no longer necessary, and the privacy of the person is safeguarded whilst simultaneously taking their interests and instructions into consideration.

Standardisation of the informed consent process: the process of obtaining declarations of consent could be standardised using an ethical avatar. The current plurality and complexity of different informed consent documents could be counteracted using such an internationally applicable, standardised instrument as the ethical avatar.

Advantage: The international distribution and the understanding of such documents would be simplified, and an international vocabulary and approach would be possible, greatly facilitating international cooperation.

Dynamic patient advance directive: The avatar could perform a support function in the event of persons being unable to express themselves. Should a person be in a coma or in a similar situation in which they are not capable of speaking for themselves, a correspondingly trained ethical avatar of the person could be of great assistance to relatives or legal guardians if they could survey said avatar instead of the person with regard to said person's wishes, interests and moral attitudes.

Advantage: The person concerned can rely on the fact that, if they themselves are incapacitated, the ethical avatar that they have trained can anticipate decisions in their interests.

Unpredicted future fields of research/areas of application: If the avatar is trained more broadly, it can also learn more general moral attitudes/values/principles of the corresponding person aside from specific questions of "informed consent", and anticipate answers even to questions that go beyond those of "informed consent".

Advantage: Rapid participation in new fields of research is made possible, with maximum use of existing cell donations.

Stratification of cohorts for biomedical research: The avatar presented here is capable of acting on behalf of a patient/subject, without releasing their sensitive data. Here, use may be made in particular of the technique described in DE 10 2019 135 380.7 ("Method and data processing device for processing genetic data", unpublished on the priority date of the present disclosure), in which searches can be performed in inaccessible data (such as the genetic information of a person) in an encrypted manner (by way of hashes) without the need for all of the information of the data to be disclosed. DE 10 2019 135 380.7 is incorporated by reference into the present disclosure, in particular with regard to the processing of genetic data. In this case, the avatar would have access to the corresponding hashes and could answer yes/no to questions posed, without having to know the encrypted information. This service would be of great advantage in particular in the assembly of patient/subject cohorts with particular common characteristics. For example, cell lines whose donors have specific, for example genetic, commonalities are often required for research objectives. In this case, the corresponding avatars could, in response to a query, confirm or else not confirm the suitability of the cell lines whose donor said avatars represent, without revealing the genetic information of their real counterpart.

The search for suitable patients/subjects could advantageously take place very quickly (answering of questions relating to specific genetic characteristics of a person), and the avatar could furthermore assist in making the preselection without disclosing the underlying sensitive data of the corresponding person.

Advantage: Safeguarding of the protection of sensitive data whilst corresponding questions are simultaneously answered, and rapid stratification of cohorts for the research, which has hitherto been possible only with great effort and great expenditure of time.

Synthetic biology: In the future, it may become possible for synthetic biological units, cells or organoids to be developed from genetic information alone—in this case, too, the ethical avatar would be conceivable as a representative entity between real persons (to whom the genetic information pertains) and research organisations. The avatar could, on behalf of the person, express consent or prohibitions with regard to what may or may not be created synthetically.

Advantage: In new fields of research and areas of application, the person is represented whilst protection of their identity is safeguarded, and questions can be answered quickly and reliably by the advisory avatar on behalf of the person concerned.

3. Use in the context of application of law

Assistance in assessing the accountability of a person: The question of whether a person is correspondingly accountable in respect of a law is dependent inter alia on how consistent their opinions are and whether their opinions have changed very often, and in a contradictory manner, in recent time. All of this can be implemented by way of an avatar which knows not only the present opinions of a person but also the "course" of their opinions and can examine the logical and, if appropriate, contradictory relationships between different opinions. The avatar could be an aid for the justice system and psychological experts to assess the mental state of a person. This could also be relevant for psychological assessment in a medical context: Inconsistencies within opinions could be an indication of increasing confusion/dementia of the person.

Advantage: Experts would not only be provided with the present state of a person for assessment but could also consider the course of their opinions over time, or the dynamics of their opinions over time.

4. Exemplary embodiments for the control of technical equipment

Use for technical equipment: Avatars could assist technical equipment in implementing the desires and interests of their users: for example by controlling filter systems in various Internet search engines such that only the desired content is displayed to the person, and other content is excluded; avatars could also perform custodial functions for minors by ensuring that no content unsuitable for minors is displayed to the minors.

Facilitation of targeted use of technical equipment in a manner suited to the desires/interests and moral attitudes of the user Moral implementation in self-driving cars: In the search for suitable moral systems for self-driving cars, common-sense solutions have hitherto been sought (implementing the average moral attitude), but it would also be possible for any driver to implement their own moral attitude in their self-driving vehicle, specifically with the aid of their ethical avatar. The avatar then functions as an individual conscience of the vehicle, like the human driver in non-self-driving cars.

Advantage: The driver does not have to submit to the dictum of average moral attitudes but can (self-evidently within the scope of what is legal) implement their personal ethical values in a road traffic context (as they would when driving manually).

5. Other exemplary embodiments

Administration/safeguarding of the access key to pseudo-anonymised personal data: To protect the personal rights and the privacy of persons, their data are, in many areas of application, protected by encryption. Here, the administration of this key is of great importance. Forgetfulness or carelessness of the persons can result in loss of this access key. An ethical avatar could assist here in safeguarding this key for the corresponding person and protecting said key against access by unauthorised parties.

Advantage: The responsibility of the person is assisted by the aid of the ethical avatar, the key would be professionally administered and safeguarded, and loss is made unlikely.

Monitoring of data protection: The avatar constitutes a link in the communication between persons and (medical) organisations and/or research institutions.

Advantage: Direct contact with the person is not necessary, and their identity remains protected whilst simultaneously allowing the maximum opportunity for participation in questions relating to them and their interests. Furthermore, the avatar can answer questions without having to reveal sensitive data (see above).

Provision of additional moral-philosophical competencies: The ethical avatar not only has access to the learned values/moral attitudes/principles of the physical person but also has further-reaching general moral-philosophical knowledge (in a separate storage shared with other avatars). During the training conversation with the person, the ethical avatar can use this knowledge to sensitise said person to further-reaching moral questions and survey said person more intelligently. In this way, the avatar would be more than a purely receiving entity that merely learns the attitudes of the person. It would furthermore be an understanding counterpart with its own moral competencies, which it however uses only during the process of training by the person. After the training, when answering questions regarding the moral attitude of its real person, said avatar would adhere to the statements made by the person without accessing its own general moral-philosophical knowledge.

Advantage: Many persons are not initially aware of the significances of their moral attitudes—moral competencies of the ethical avatar allow the persons to be intelligently surveyed during the training conversation without undermining their decision-making autonomy. Furthermore, interested persons can in this way (by conversation with their avatar) be motivated to contemplate response characteristics, such as moral response characteristics, and train themselves in their own moral judgements.

The features of the invention disclosed in the description above, in the drawings and in the claims may be of importance both individually and in combination or sub-combination for realising the invention in its various embodiments.

What is claimed is:

1. A method for processing search queries from a research entity directed at a database containing at least one of medical sample data and samples from a multiplicity of samples of persons, comprising:

entering a search query, with a request profile directed at retrieving at least one sample with sample data that have predetermined queried search parameters, into a learning AI processor device, searching for at least one selected sample using the AI processor device, the at least one selected sample satisfying the request profile at least with a specified probability, wherein the AI processor device learns by way of at least one of separate training and evaluating the search queries directed at the AI processor device, by an output device of the AI processor device, outputting identification data of the at least one selected sample, and by the output device of the AI processor device, outputting additional rating search parameters that match the search query such that a group of samples that have an increased probability of successfully satisfying the request profile are selectable for independently outputting an evaluation regarding which parameters of the sample data could be of interest for research by the research entity.

2. The method according to claim 1, wherein the AI processor device is used to search for a group of selected samples, all selected samples satisfying the request profile at least with the specified probability.

3. The method according to claim 2, wherein the identification data of the group of selected samples are output with ranking information (placement information) that assigns each of the selected samples a hit probability of the request profile being satisfied.

4. The method according to claim 1, wherein the rating search parameters include at least one of a genetic profile, data relating to clinical treatments, pre-existing diseases, familial predispositions to disease, personal diagnostic results, characteristics of living habits, eating habits, consumer behaviour, sport and physical activity characteristics, data relating to consumption of drugs or other intoxicants, data relating to medication intake, data relating to radiation exposure, epigenetic data, geographical information, age, gender, ethnicity, allergies and psychiatric disorders.

5. The method according to claim 1, wherein the request profile is directed at retrieving a group of samples with sample data, the persons associated with the group of samples forming a subject cohort.

6. The method according to claim 1, wherein the AI processor device processes at least one of information from specialist literature, commercial market information from the industrial sector and information from approvals databases relating to pharmaceutical products.

7. The method according to claim 1, further comprising: converting the search query into a fragmented search query using a coding function.

8. The method according to claim 1, further comprising: requesting consent of the associated persons to the use of at least one of data and samples.

9. The method according to claim 8, wherein the request for consent is responded to by at least one of using at least one of questionnaires and informed consent documents and an avatar apparatus.

10. The method according to claim 1, further comprising: outputting information relating to at least one of pharmaceutical products, diseases, research results and recommended actions.

11. A search platform apparatus that is configured to process search queries from a research entity directed at a database containing at least one of medical sample data and samples from a multiplicity of samples of persons, comprising:

an input device that is adapted to receive a search query with a request profile directed at retrieving at least one sample with sample data that have predetermined queried search parameters, a learning AI processor device that is coupled to the input device and is adapted to search for at least one selected sample, the at least one selected sample satisfying the request profile at least with a specified probability, and an output device that is adapted to output identification data of the at least one selected sample, wherein the AI processor device is adapted to learn by way of at least one of separate training and evaluating the search queries directed at the AI processor device and to generate and output via the output device additional rating search parameters that match the search query such that a group of samples that have an increased probability of successfully satisfying the request profile are selectable for independently outputting an evaluation regarding which parameters of the sample data could be of interest for research by the research entity.

12. The search platform apparatus according to claim 11, wherein the AI processor device is adapted to search for a group of selected samples, all selected samples satisfying the request profile at least with the specified probability.

13. The search platform apparatus according to claim 12, wherein the AI processor device is adapted to generate the identification data of the group of selected samples including ranking information that assigns each of the selected samples a hit probability of the request profile being satisfied.

14. The search platform apparatus according to claim 11, wherein the rating search parameters include at least one of a genetic profile, data relating to clinical treatments, pre-existing diseases, familial predispositions to disease, personal diagnostic results, characteristics of living habits, eating habits, consumer behaviour, sport and physical activity characteristics, data relating to consumption of drugs or other intoxicants, data relating to medication intake, data relating to radiation exposure, epigenetic data, geographical information, age, gender, ethnicity, allergies and psychiatric disorders.

15. The search platform apparatus according to claim 11, wherein the AI processor device is adapted to process at least one of information from specialist literature, commercial market information from the industrial sector and information from approvals databases relating to pharmaceutical products.

16. The search platform apparatus according to claim 11, further comprising a coding device that is adapted to convert the search query into a fragmented search query using a coding function.

17. The search platform apparatus according to claim 11, wherein the AI processor device is adapted to request consent of the associated persons to the use of at least one of data and samples.

18. The search platform apparatus according to claim 17, wherein the AI processor device is adapted to request consent by at least one of using at least one of questionnaires and informed consent documents, and an avatar apparatus.

\* \* \* \* \*